United States Patent [19]
Das et al.

[11] Patent Number: 6,143,504
[45] Date of Patent: Nov. 7, 2000

[54] METHODS AND COMPOSITIONS FOR THE DIAGNOSIS OF FRAGILE X SYNDROME

[75] Inventors: Soma Das; David H. Ledbetter, both of Chicago, Ill.

[73] Assignee: Arch Development Corporation, Chicago, Ill.

[21] Appl. No.: 09/429,499

[22] Filed: Oct. 27, 1999

[51] Int. Cl.[7] .............................. C07H 21/04; C12Q 1/68; C12P 19/34
[52] U.S. Cl. ............................ 435/6; 536/22.1; 536/24.3; 435/91.2
[58] Field of Search ...................... 435/6, 91.2; 536/22.1, 536/24.3

[56] References Cited

U.S. PATENT DOCUMENTS 5,658,764   8/1997   Pergolizzi et al. ...................... 435/91.2

OTHER PUBLICATIONS

Annemieke et al., "Identification of a gene (FMR–1) containing a CGG repeat coincident with a breakpoint cluster region exhibiting length variation in Fragile X Syndrome," *Cell*, 65:905–914, 1991.
Bell et al., "Physical mapping across the Fragile X: hypermethylation and clinical expression of the Fragile X Syndrome," *Cell*, 64:861–866, 1991.
Clark et al., "High sensitivity mapping of methylated cytosines," *Nuc. Acids. Res.*, 22:2990–2997, 1994.
Eichler et al., "Fine structure of the human FMR1 gene," *Hum. Mol. Genet.*, 2:1147–1153, 1993.
Frommer et al., "A genomic sequencing protocol that yields a positive display of 5–methylcytosine residues in individual DNA stands," *Proc. Natl. Acad. Sci. USA*, 89:1827–1831, 1992.
Fu et al., "Variation of the CGG repeat at the Fragile X site results in genetic instability: resolution of the Sherman paradox," *Cell*, 67:1047–1058, 1991.
Haddad et al., "A PCR–based test suitable for screening for Fragile X Syndrome among mentally retarded males," *Hum. Genet.*, 97:808–812, 1996.
Hagerman et al., "Girls with Fragile X Syndrome: physical and neurocognitive status and outcome," *Pediatrics*, 89:395–400, 1992.
Hansen et al., "Methylation analysis of CGG sites in the CpG island of the human FMR1 gene," *Hum. Mol. Genet.*, 1:571–578, 1992.
Herman et al., "Methylation–specific PCR: A novel PCR assay for methylation status of CpG islands," *Proc. Natl. Acad. Sci. USA*, 93:9321–9826, 1996.
Hirst et al., "Two new cases of FMR1 deletion associated withmental impairment," *Am. J. Hum. Genet.*, 56:67–74, 1995.
Hornstra et al., "High resolution methylation analysis of the FMR1 gene trinucleotide repeat region in Fragile X Syndrome," *Hum. Mol. Genet.*, 2:1659–1665, 1993.
Kremer et al., "Mapping of DNA instability at the Fragile X to a trinucleotide repeat sequence p(CCG)$n$," *Science*, 252:1711–1714, 1991.

(List continued on next page.)

*Primary Examiner*—Jeffrey Fredman
*Assistant Examiner*—Arun Chakrabarti
*Attorney, Agent, or Firm*—Fulbright & Jaworski L.L.P.

[57] ABSTRACT

The present invention relates generally to the field of diagnostics. More particularly, it concerns the use of methylation-specific PCR in order to identify those males having Fragile X syndrome. The present invention provides a method in which amplification specific for the methylated FMR1 sequence is observed in all individuals with a full mutation, while all normal and premutation individuals show only amplification specific for the unmethylated sequence, thus allowing affected and unaffected males to be distinguished. A full mutation in the presence of mosaicism also may detectable by this method. Thus, methylation-specific PCR is demonstrated as a rapid and reliable tool for the diagnosis of fragile X.

24 Claims, 2 Drawing Sheets

```
UNTREATED SEQUENCE (ANTISENSE STRAND; SEQ ID NO:1)

3´-CGGCCAAGGGTCGTCGCGCGTACGCGCGCGAGGGTCC...CAGTCCGCGAGTCGAGGCAAAGCC

...GCGCCCGCCGCCGCCACTGCCTC-5´

TREATED METHYLATED SEQUENCE (FRAGILE X AFFECTED; SEQ ID NO:2)

FX-BS-for
    ──────────────────▶ v     v v      v v v               v      v v      v
3´-TGGCTAAGGGTTGTTGCGCGTATGCGCGCGAGGGTTT...TAGTTTGCGAGTTGAGGCAAAGCT
        FX-BS-rev
    ◀────────── v v   v v v   v
...GCGCTTGCTGCTGCTATTGCTTT-5´
```

OTHER PUBLICATIONS

Kubota et al., "Methylation–specific PCR simplifies imprinting analysis," *Nature Genet.*, 16:16–17, 1997.

Larsen et al., "High–throughput analysis of Fragile X $(CGG)_n$ alleles in the normal and premutation range by PCR amplification and auotomated apillary electrophoresis," *Human Genetics*, 100:564–568 1997.

Oberle et al., "Instability of a 550–base pair DNA segment and abnormal methylation in Fragile X Syndrome," *Science*, 252:1097–1102, 1991.

Papp et al., "Strategies for amplification of trinucleotide repeats: Optimization of Fragile X and androgen receptor PCR," *Molecular diagnosis*, 1:59–64, 1996.

Pergolizzi et al., "Detection of full Fragile X mutation," *Lancet*, 339:217–218, Feb. 1992.

Pieretti et al., "Absence of expression of the FMR–1 gene in Fragile X Syndrome," *Cell*, 66:1–20, 1991.

Richards et al., "Fragile X Syndrome: genetic localisation by linkage mapping of two microsatellite repeats FRAXACI and FRAXAC2 which immediately flank the Fragile site," *J Med Genet.* 28(12):818–823, 1991.

Rousseau et al., "Direct diagnosis by DNA analysis of the Fragile X Syndrome of mental retardation ," *N. Engl. J. Med.*, 325:1673–1681, 1991.

Sutcliffe et al., "DNA methylation represses FMR–1 transcription in Fragile X Syndrome," *Hum. Mol. Genet.*, 397–400, 1992.

Wang et al., "A rapid, non–radioactive screening test for Fragile X mutations at the FRAXA and FRAXE loci," *J. Med Gene*, 32:170–173, 1995.

Willemsen et al. "Rapid antibody test for Fragile X Syndrome," *Lancet*, 345:1147–1148, 1995.

UNTREATED SEQUENCE (ANTISENSE STRAND; SEQ ID NO:1)

3'-CGGCCAAGGGTCGTCGCGCGTACGCGGCGAGGGTCC...CAGTCCGCGAGTCGAGGCAAAGCC

...GCGCCCGCCGCCACTGCCTC-5'

TREATED METHYLATED SEQUENCE (FRAGILE X AFFECTED; SEQ ID NO:2)

FX-BS-for →

3'-TGGCTAAGGGTTGTTGCGCGTATGCGCGCGAGGGTTT...TAGTTTGCGAGTTGAGGCAAAGCT

FX-BS-rev ←

...GCGCTTGCTGCTGCTATTGCTTT-5'

TREATED METHYLATED SEQUENCE (FRAGILE X UNAFFECTED; SEQ ID NO:3)

NM-BS-for →

NM-BS-rev ←

3'-TGGTTAAGGGTTGTGTGTATGTGTGTGAGGGTTT...TAGTTTGTGAGTTGAGGTAAAGTT

...GTGTTTGTTGTGTTATTGTTTT-5'

*FIG. 1B*

METHODS AND COMPOSITIONS FOR THE DIAGNOSIS OF FRAGILE X SYNDROME

CROSS REFERENCE TO RELATED APPLICATION

This application claims the benefit of priority from U.S. Provisional Application Ser. 60/105,892, filed Oct. 27, 1998.

BACKGROUND OF THE INVENTION

1. Field of the Invention

The present invention relates generally to the fields of diagnostics. More particularly, it concerns the use of methylation-specific PCR in order to identify those individuals having Fragile X syndrome.

2. Description of Related Art

The fragile X syndrome is the most common inherited form of mental retardation and developmental disability. This condition afflicts approximately 1 in 2500 males and 1 in 5000 females. Males with fragile X syndrome usually have mental retardation and often exhibit characteristic physical features and behavior (Hagerman and Silverman, 1992; Warren and Nelson, 1994). Perhaps the most debilitating clinical feature noted in individuals with Fragile X is that of behavior, these characteristics include behavior similar to autism and attention deficit disorder, obsessive-compulsive tendencies, hyperactivity, slow development of motor skills and anxiety fear disorder. When these disabilities are severe and occur simultaneously, the condition is sometimes described as autism, and may be associated with any degree of intelligence. Minorities of individuals with fragile X have autism. Many more have some of the above features. Particularly common in fragile X (and much less so in other conditions) is the combination of a likable, happy, friendly personality with a limited number of autistic-like features such as hand-flapping, finding direct eye contact unpleasant, and some speech and language problems.

Generally speaking, the problems experienced by girls and women with fragile X are similar to those of boys and men. Girls and women with more average intellectual functioning may still have large discrepancies between different ability areas and may show similar concentration problems with impulsiveness, distractibility and difficulty sticking to tasks even if they are not overactive. Shyness and anxiety in social situations can occur.

Fragile X is an X chromosome-linked condition that is characterized by a visible constriction near the end of the X chromosome, at locus q27.3, and there is a tendency for the tip of the X-chromosome to break off under certain conditions in tissue culture. The pattern of inheritance of this condition is atypical of that associated with X-linked conditions. In typical X-linked genetic defects, there is a 50% probability that the male offspring of a female carrier will be afflicted by the defect. Additionally, all males who carry the abnormal gene are afflicted by the X-linked disorder in the typical pattern. Furthermore, since females have two X chromosomes, they normally do not suffer the effects of a single damaged X chromosome. In fragile X syndrome, however, carrier males are phenotypically normal. Certain individuals are carriers of fragile X in that they have a premutation in the FMR1 gene but do not show symptoms of fragile X. Carrier men (transmitting males) pass the premutation to all their daughters but none of their sons. Each child of a carrier woman has a 50% chance of inheriting the gene. The fragile X premutation can be passed silently down through generations in a family before a child is affected by the syndrome. Moreover, about one-third of the females inheriting the fragile X chromosome are afflicted with the disease. Daughters of carrier males are generally non-expressing carriers, but may have afflicted sons. Afflicted daughters occur more frequently among the offspring of carrier mothers than among the offspring of carrier fathers (Brown, 1990).

The genomic region associated with this condition has been identified (Oberle et al., 1991; Kremer et al., 1991; Bell et al., 1991). Researchers have sequenced a cDNA clone derived from this region, called FMR1 (Verkerk et al., 1991). FMR1 has been recognized since 1991 as the gene that causes fragile X (Verkerk et al., 1991; Richards et al., 1991; Eichler et al., 1993; Hirst et al., 1995). The fragile X syndrome is predominantly caused by a large expansion of a CGG trinucleotide repeat in the promoter region of the FMR1 gene, which is associated with methylation and down regulation of transcription. However, it appears that the mutation that ultimately results in the fragile X phenotype occurs in stages. In the early stages, the gene is not fully defective; rather there is a "pre-mutation" of the gene. Carriers of the pre-mutation have a normal phenotype. A further expansion of the premutation occurs in carrier females-that produces the phenotype in their offspring. In individuals who have fragile X syndrome, a defect in FMR1 (a full mutation) of a CGG trinucleotide repeat correlates with methylation of the gene.

Individuals who are not carriers have approximately 30 CGG repeats in their FMR1. Carriers, however, have between about 50 and about 200 CGG repeats. This amplification of the FMR1 CGG sequence is the pre-mutation. Patients with fragile X syndrome have an expansion to the full mutation, which is greater than 200 repeats (Verkerk et al., 1991; Kremer et al., 1991), with as many as several thousand CGG repeats having been reported in afflicted individuals (Oberle et al., 1991). A CpG island, located upstream of the CGG repeat region is methylated when the number of CGG repeats is above a threshold of about 200 copies (Oberle et al., 1991; Kremer et al., 1991, Bell et al., 1991). This methylation results in an inactivation of the gene and silencing of gene transcription which is believed to result in the fragile X phenotype (Verkerk et al., 1991; Oberle et al., 1991; Sutcliffe et al., 1992). Most affected individuals do not express the FMR-1 mRNA (Pieretti et al., 1991). Full mutations also can exist with premutation and normal alleles, and such individuals are known as "mosaic" (Verkerk et al., 1991; Kremer et al., 1991).

A molecular diagnosis of this disorder is based on repeat size and methylation analysis of the FMR1 gene. As methylation has a direct effect on the fragile X phenotype and does not always correlate with repeat expansion, its analysis is an important part of fragile X diagnostics. Molecular testing of the fragile X syndrome is predominantly performed by Southern blot (Rousseau et al., 1991) and/or PCR analysis (Fu et al., 1991; Pergolizzi et al., 1992; U.S. Pat. No. 5,658,764). The advantage of Southern analysis is that methylation status is obtained in addition to repeat expansion. The main disadvantages of this technique are the time taken to perform the procedure, the large amounts of DNA necessary for analysis, and the use of radioisotopes. In PCR-based methods, carriers of the fragile X genotype are identified based on molecular structure of the gene defect. These methods determine whether the number of CGG repeats in the test individual's X-chromosome are characteristic of a normal, carrier or afflicted person. The PCR test, which provides information on repeat size, usually employs radioactivity based assays and has shown limited success in diagnosing full mutations. Other PCR based methods that serve as rapid screening tools for fragile X have been described (Wang et al., 1995; Haddad et al., 1996; Larsen et al., 1997). These methods, however, depend on the non-amplification of a full mutation as an indicator of fragile X and require confirmation by Southern analysis, additionally, these assays are unable to detect a full mutation in the presence of mosaicism.

Additional methods for the diagnosis of fragile X syndrome use microscopy, in which an afflicted individual's chromosomes are examined after cell growth and treatment in tissue culture. The X chromosome is examined to ascertain whether it was characteristically constricted, or had a broken tip. This method is both costly and unreliable. A more recent approach to the identification of fragile X is by assay of FMRP, where a lack of protein is indicative of fragile X (Willemsen et al., 1995). This is a promising technique particularly for large screening studies; however it cannot be used to identify premutations and has a high false negative rate in females.

There currently is no cure for fragile X syndrome, although appropriate education and medications can help maximize the potential of each child. However, most boys and many girls remain significantly affected throughout their lives. The cost to society for treatment, special education, and lost income is staggering. Diagnoses of this syndrome will be helpful in designing appropriate therapies and counseling for affected individuals and carriers of the syndrome. There still exists a need for rapid and reliable assays for Fragile X syndrome to aid those suffering from or carrying the disorder.

SUMMARY OF THE INVENTION

The present invention provides a reliable tool for the diagnosis of fragile X syndrome in males. More particularly, the present invention provides a method for determining the methylation state of an FMR1 gene promoter of a male subject comprising the steps of (a) denaturing a DNA sample from the subject; (b) subjecting the denatured DNA to bisulfite modification; (c) amplifying the DNA using primers pairs having the sequences ACCGATTCCCAA-CAACGCGCATA and TTTCGTTATCGTCGTCGTTCGC, and ACACACATACACACACTCCCAAA and TTGAAATGGAGTTGAGTGTTTGAT; and (d) detecting amplification products from step (c).

In specific embodiments, the method further may comprise the step, before step (a), of obtaining a DNA sample from the subject. In particular embodiments, the sample is blood, amniotic fluid or a buccal smear. In specific embodiments, the denaturing comprises treatment with NaOH and heat. In particular embodiments, the bisulfite modification comprises treatment with hydroquinone and sodium bisulfite, followed by treatment with NaOH. In certain embodiments, the denaturing comprises treatment with NaOH and heat. In certain embodiments, it is contemplated that the method further comprises the step of purifying the bisulfite modified DNA. In particular embodiments, the amplification comprises PCR. In more defined embodiments, the PCR comprises 35 cycles at 94° C. for 30 seconds, 64° C. for 30 seconds and 72° C. for 30 seconds, followed by a final extension at 72° C. for 10 minutes. In certain embodiments, the amplification products are unlabeled. In alternative embodiments, the amplification products are labeled with a detectable label.

More particularly, the label may be is radioactive, fluorescent, chemilluminescent or colorimetric. In certain embodiments, the detection comprises gel electrophoresis and visualization of size-separated PCR products. In other embodiments, the primer may comprise an additional sequence that is not complementary to a region of FMR1 gene promoter. In more defined embodiments, the non-complementary region comprises a restriction enzyme site.

The present invention further provides an isolated primer comprising the sequence ACCGATTCCCAACAACGCG-CATA. In other embodiments, the present invention provides an isolated primer comprising the sequence TTTCGT-TATCGTCGTCGTTCGC. In yet another embodiment, the present invention provides an isolated primer comprising the sequence ACACACATACACACACTCCCAAA. In still a further embodiment, the invention provides an isolated primer comprising the sequence TTGAAATGGAGT-TGAGTGTTTGAT.

Also contemplated by the present invention is a set of two primer pairs comprising the following sequences: ACCGAT-TCCCAACAACGCGCATA and TTTCGTTATCGTCGTCGTTCGC, and ACACACATA-CACACACTCCCAAA and TTGAAATGGAGTTGAGT-GTTTGAT.

Also provided by the present invention is a kit comprising, in suitable container means, primer pairs comprising the following sequences: ACCGATTCCCAA-CAACGCGCATA and TTTCGTTATCGTCGTCGTTCGC, and ACACACATACACACACTCCCAAA and TTGAAATGGAGTTGAGTGTTTGAT. In certain embodiments, the kit further may comprise a thermostable DNA polymerase. In other preferred embodiments, the kit further may comprise sodium bisulfite and hydroquinone. In additional embodiments, the kit also comprises a DNA denaturing agent. In other embodiments, the kit may also include dNTP's.

Following longstanding patent law convention, the word "a" and "an", when used in conjunction with the word comprising, mean "one or more" in this specification, including the claims.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

1. The Present Invention

Figure 1A:
FIG. 1. Bisulfite modification of the 5' untranslated region of the FMR1 gene. Depicted is the antisense strand from nucleotides 13551 to 13803 (Genbank accession no. L29074). Changes in nucleotide sequence between the bisulfite treated and untreated versions are underlined. Changes in nucleotide sequence between the methylated and unmethylated versions after bisulfite treatment are indicated by the arrowhead. Note that those residues denoted by the arrowhead reflect cytosines that are methylated in fragile X affected as opposed to unaffected individuals. Primers designed to the bisulfite modified sequence contain nucleotides that differ between the methylated and unmethylated versions of the FMR1 gene to allow for their discrimination. Primers also contain nucleotide sequence that allows for the discrimination between the treated and untreated versions of the FMR1 gene. The sequences in this figure are given in SEQ ID NO:1, SEQ ID NO:2, SEQ ID NO:3 SEQ ID NO:4 SEQ ID NO:5 SEQ ID NO:6 SEQ ID NO:7, SEQ ID NO:8 and SEQ ID NO:9.

The present invention describes a PCR-based method for the analysis of methylation of the FMR1 gene, which involves bisulfite treatment of DNA prior to amplification. Methylation-specific PCR of the present invention is a rapid and reliable tool for the diagnosis of fragile X males.

Methylation-PCR is a rapid assay that can be completed in two days and requires very little DNA for analysis, two important factors for prenatal diagnosis. Other advantages of the test are that it is non-radioactive, cost and labor efficient, making it amenable for routine diagnostics and screening studies. The methylation-PCR assay produces amplification specific for either presence or absence of methylation (or both), and thus provides an advantage over the other screening methods described above, where a positive result is dependent on an absence of product. A possible disadvantage of the methylation-PCR test is the inability to analyze females, as the inactive X chromosome will always result in amplification specific for the methylated FMR1 gene. However, the majority of tests for fragile X are initiated from males with mental retardation. It may be desirable to perform methylation-PCR along with amplification by conventional PCR across the triplet repeat for all male samples sent for fragile X testing, as this will allow normal, premutation and full mutation males to be identified. Female samples are best analyzed by conventional Southern blot or PCR analysis.

Methylation-PCR provides an alternative method for the molecular testing of fragile X and can be used to identify affected and unaffected males even in the presence of mosaicism. This is an important factor, as about 20% of affected fragile X individuals are mosaic (Rousseau et al., 1991). Two types of mosaicism have been described in fragile X, those where full mutations are present with premutation or normal alleles (Verkerk et al., 1991; Oberle et al., 1991), as well as the rarer instance of full mutations mosaic for methylation (Rousseau et al., 1991). In a retrospective study, two cases out of 100 samples where methylation was not identified fall into the second category: both were borderline premutation/full mutation individuals with less than 10% methylation. Both patients were ascertained by analysis of families with a positive history of fragile X syndrome. They had none of the physical features characteristic of fragile X and demonstrated only cognitive features of very mild fragile X. All other methylation mosaic individuals in the study had detectable methylation by the assay. The methylation-PCR assay cannot distinguish between an individual with a full mutation and an individual mosaic for a full mutation/premutation. Male individuals with a full mutation, may be further tested by Southern analysis to determine if mosaicism is present.

Fifty-two normal and 48 affected (premutation or mosaic) males were analyzed in a blinded study by this method. A prospective study of 30 males suspected of fragile X also was performed. Amplification specific for the methylated FMR1 sequence was readily observed in all individuals with a full mutation, while all normal and premutation individuals showed only amplification specific for the unmethylated sequence, thus allowing affected and unaffected males to be distinguished. A full mutation in the presence of mosaicism also was detectable by this method.

The present invention also describes a PCR assay that tests for methylation to diagnose the fragile X syndrome. Using this assay, FX-specific amplification (amplification specific for the methylated sequence) is seen in full mutation individuals and not in normal or premutation individuals. The latter two groups of patients show only NM-specific amplification (amplification specific for the unmethylated sequence) in over 70 normal males tested. Some amount of NM-specific amplification is seen in most full mutation carriers as well. This does not appear to be due to non-specific priming, as it is not seen in all cases and as other NM-specific primers tested have given similar results. This may either reflect a low level of mosaicism and/or a low level of unmethylated FMR1 sequence in fragile X individuals not detectable by Southern analysis. The finding of different levels of NM-specific amplification in full mutation carriers is consistent with the observation of expression of some Fragile X mental retardation 1 protein (FMRP) in a proportion of affected males (Willemsen et al., 1995).

The use of methylation-PCR to distinguish between affected and unaffected males with fragile X demonstrates the value of this method as a diagnostic and screening tool for genetic diseases that involve methylation. Methods and compositions relating the use of this assay for the diagnostic purposes are described in further detail herein below.

2. The FMR1 Gene and Fragile X Syndrome

The fragile X mental retardation gene, FMR1, is well known to those of skill in the art, and FMR1 nucleic acid sequences may be found at computerized databases known to those of ordinary skill in the art. One such database, for example, is the National Center for Biotechnology Information's Genbank database (http://www.ncbi.nlm.nih.gov/). Non-limiting examples of FMR1 sequences include Genbank accession No. Q06787; Genbank accession No L29074; Genbank accession No M67468; Genbank accession No A39530, each incorporated herein by reference.

The present invention provides methods for the diagnosis and prognosis of fragile X syndrome in individuals suspected of having fragile X. One embodiment of the instant invention comprises a method for detecting variation in CpG islands of FMR1. The methods may use a biological sample in analysis. The biological sample can be any tissue or fluid. In a particular embodiment, the fluid used is blood. In genetic testing amniotic fluid and blood may be assayed. Skin tissue, buccal smears, hair root follicles or any other material from which DNA may be extracted also may be used.

Nucleic acids are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or by comparision with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal individuals (normal reference group) and individuals that have fragile X syndrome (positive reference group). In this way, it is possible to correlate the amount or kind of FMR1 mutation.

3. Methylation Specific PCR

The present invention describes a PCR-based method for the detection of methylation in fragile X. This method is based on the bisulfite modification of DNA where unmethylated cytosine residues are converted to uracil, while methylated residues remain unconverted (Frommer et al., 1992; Clark et al., 1994). The subsequent change in the sequence of the FMR1 promoter between fragile X affected and unaffected individuals after bisulfite treatment is monitored by PCR. The use of methylation-specific PCR for the detection of methylation in tumor suppressor genes (Herman et al., 1996) and genetic disorders of imprinting such as Prader-Willi syndrome and Angelmans syndrome (Kubota et al., 1997) have previously been demonstrated. The present invention demonstrates the successful identification of affected and unaffected males with fragile X by methylation-specific PCR.

a. Conventional PCR™

The polymerase chain reaction (referred to as PCR™) has been extensively described in U.S. Pat. Nos. 4,683,195, 4,683,202 and 4,800,159, and in Innis et al., 1990, each incorporated herein by reference.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

Other nucleic acid amplification procedures include transcription-based amplification systems (TAS), including nucleic acid sequence based amplification (NASBA) and 3SR (Kwoh et al., 1989; Gingeras et al, PCT Application WO 88/10315). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double-stranded DNA molecules are heat denatured again. In either case the single stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double-stranded DNA, and then transcribed once again with an RNA polymerase such as T7 or SP6. The resulting products, whether truncated or complete, indicate target specific sequences.

b. Methylation-specific PCR™

Methylation specific PCT™ combines the use of methylation sensitive enzymes and PCR™ (Singer-Sam et al., 1990). After digestion of DNA with the enzymes, PCR amplification of the primers flanking a restriction site occurs only if the DNA cleavage has been prevented by methylation (Razin and Cedar, 1991; Stoger et al., 1993). The chemical modification of cytosine to uracil by bisulfite treatment provides a useful modification of traditional PCR techniques. Using this modification, the need for restrictions enzymes is circumvented (Frommer et al., 1992).

In this reaction, all the cytosines in a given nucleic acid sequence are converted to uracil but those cytosines that are methylated (5-methylcytosine) are resistant to this modification and remains as cytosine (Wang et al., 1980). The sequence under investigation is then amplified by PCR with two sets of strand-specific primers to yield a pair of fragments, one from each strand, in which all uracil and thymine residues have been amplified as thymine and only 5-methylcytosine residues have been amplified as cytosine. The PCR products can be sequenced directly to provide a strand-specific average sequence for the population of molecules or can be cloned and sequenced to provide methylation maps of single DNA molecules (Frommer et al., 1992).

A methylation-specific PCR has been described by Herman et al. (1996), which can rapidly assess the methylation status of virtually any group of CpG sites within a CpG island, independent of the use of methylation-sensitive restriction enzymes. This assay entails initial modification of DNA by sodium bisulfite, converting all unmethylated, but not methylated, cytosines to uracil, and subsequent amplification with primers specific for methylated versus unmethylated DNA. This assay requires only small quantities of DNA, is sensitive to 0.1% methylated alleles of a given CpG island locus, and can be performed on DNA extracted from paraffin-embedded samples. Methylation-specific PCR eliminates the false positive results inherent to previous PCR-based approaches which relied on differential restriction enzyme cleavage to distinguish methylated from unmethylated DNA.

The following is a brief description of the methylation specific PCR method. In bisulfite modification, an appropriate amount of DNA (e.g., 1 $\mu$g in a 50 $\mu$l volume) is denatured by adding 0.2M NaOH and incubating at 37° C. for 10 minutes. For samples with nanogram quantities of DNA, a carrier DNA may be added to spike the sample before the modification reaction. The DNA may be extracted from any tissue of the individual being examined, for example, the DNA may be extracted from blood, amniotic fluid and the like.

30 $\mu$l of 10 mM hydroquinone and 520 $\mu$l of 3M sodium bisulfite at pH 5 are added and the samples are incubated under mineral oil at 50° C. for 16 hours. Modified DNA is then purified as described in Herman et al., 1996. The modification is completed by NaOH treatment for 5 minutes at room temperature followed by ethanol precipitation. DNA is resuspended in water and used immediately or stored at −20° C.

PCR typically employs two primers that bind to a selected nucleic acid template. The primers are combined with the other PCR reagents under conditions that induce primer extension, i.e., with four different nucleoside triphosphates (or analogues thereof), an appropriate polymerase and an appropriate buffer ("buffer" includes pH, ionic strength, cofactors, etc.) at a suitable temperature. In a PCR method where the polymerase is Taq polymerase, the buffer preferably contains 1.5–2 mM of a magnesium salt, preferably MgCl$_2$, 150–200 μM of each nucleoside, triphosphate (or analog thereof), 1 μM of each primer, preferably with 50 mM KCl, 10 mM Tris buffer at pH 8.4, and 100 μg/ml gelatin.

In specific embodiments, PCR primers are prepared from the FMR1 gene and PCR was carried out in a 50 μl volume containing 1 X PCR buffer II (Perkin-Elmer), 4.5 mM MgCl$_2$, 200 μM dNTPs, 0.5 μM NM-BS primers, 1.0 μM FX-BS primers (sequences in table 1), 1 unit of Amplitaq Gold enzyme (Perkin-Elmer) and approximately 30 ng of bisulfite-modified DNA. The polymerase was activated at 95° C. for 10 mins, and DNA amplified in a Perkin-Elmer model 9600 thermocycler for 35 cycles at 94° C. for 30s, 64° C. for 30s and 72° C. for 30s, followed by a final extension at 72° C. for 10 mins.

4. Primers and Probes

The present invention will use PCR primers designed specific for FMR-1 to be used to determine whether the gene is mutated or wild-type. The primer is preferably single stranded for maximum efficiency in amplification, but it may be double stranded. Double stranded primers are first "denatured", i.e. treated to separate its strands before being used to prepare extension products. A preferred means of denaturing double stranded nucleic acids is by heating.

a. Primer Design

The term primer, as defined herein, is meant to encompass any nucleic acid that is capable of priming the synthesis of a nascent nucleic acid in a template-dependent process. Typically, primers are oligonucleotides from about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, to about 100 bases in length, including all intermediate ranges. It will be readily understood that "intermediate ranges", as used herein, means any length or range including or between the quoted values (i.e. all integers including and between such values). A non-limiting example of such a range would be from about 10 to about 50 bases in length. Additionally, sequences greater than 100 bases or base pairs in length can be employed.

Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In the present invention, a primer needs to be sufficiently long to "prime" the synthesis of extension products in the presence of an appropriate polymerase and other reagents. The primer length depends on many factors, including the temperature and source of the primer and the use of the method. The particular length of the primer is not believed to be critical, with the primer sequence ranging from about 10 to about 25 bases. Short primer molecules generally require lower reaction temperatures to form and maintain the primer-template complexes which support the chain extension reaction. In some embodiments, the primers are labeled with radioactive species (e.g. $^{32}$P, $^{14}$C, $^{35}$S, $^{3}$H, or other isotope), with a fluorophore (including, but not limited to, rhodamine, fluorescein or GFP) or a chemiluminescent label (including, but not limited to, luciferase).

The primers used in the present method are "substantially" complementary to a nucleic acid containing the selected sequence to be amplified, i.e. the primers must bind to, or hybridize with, a nucleic acid containing the selected sequence (or its complement). Nonetheless, the primer sequence need not be an exact complement of the template. For example, a non-complementary nucleotide fragment may be attached to the 5' end of the primer, with the remainder of the primer sequence being complementary to the nucleic acid containing the selected sequence. Alternatively, one or more non-complementary bases can be interspersed into the primer, provided that the primer sequence has sufficient complementarity with the sequence of the nucleic acid containing the selected sequence to (i) hybridize therewith and (ii) support a chain extension reaction. Notwithstanding the above, primers which are fully complementary to the nucleic acid containing the selected sequence are preferred to obtain the best results.

b. Primer Synthesis

Oligonucleotide synthesis is well known to those of skill in the art, and may be performed according to standard methods. See, for example, Itakura and Riggs (1980). Various different mechanisms of oligonucleotide synthesis have been disclosed in for example, U.S. Pat. No. 4,659,774, U.S. Pat. No. 4,816,571, U.S. Pat. No. 5,141,813, U.S. Pat. No. 5,264,566, U.S. Pat. No. 4,959,463, U.S. Pat. No. 5,428,148, U.S. Pat. No. 5,554,744, U.S. Pat. No. 5,574,146, U.S. Pat. No. 5,602,244, each of which is incorporated herein by reference. Additionally, U.S. Pat. No. 4,704,362; U.S. Pat. No. 5,221,619 U.S. Pat. No. 5,583,013 each describe various methods of preparing synthetic structural genes, and are incorporated herein by reference. Chemical synthesis can be achieved by the diester method, the triester method polynucleotides phosphorylase method and by solid-phase chemistry. These methods are discussed in further detail below.

Diester Method

The basic step of the diester method is the joining of two suitably protected deoxynucleotides to form a dideoxynucleotide containing a phosphodiester bond. The diester method is well established and has been used to synthesize DNA molecules (Khorana, 1979).

Triester Method

The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purification's are done in chloroform solutions. Other improvements in the method include the block coupling of trimers and larger oligomers, the extensive use of high-performance liquid chromatography for the purification of both intermediate and final products, and solid-phase synthesis.

Polynucleotide Phosphorylase Method

This is an enzymatic method of DNA synthesis that can be used to synthesize many useful oligodeoxynucleotides (Gillam et al., 1978; Gillam et al., 1979). Under controlled conditions, polynucleotide phosphorylase adds predominantly a single nucleotide to a short oligodeoxynucleotide. Chromatographic purification allows the desired single adduct to be obtained. At least a trimer is required to start the procedure, and this primer must be obtained by some other method.

Solid-phase Methods

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic DNA synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

5. Enzymes and Reagents

The present section provides examples of enzymes and reagents used in the present invention to carry out methylation specific PCR, these include RT enzymes, DNA polymerases, RNase inhibitors and other compositions required or helpful for optimizing reaction conditions. Of course, the enzymes and reagents discussed below are exemplary and non-limiting, as it is understood that any additional enzymes or reagents that possess similar activities may substitute for those specifically described.

M-MLV Reverse Transcriptase

M-MLV (Moloney Murine Leukemia Virus Reverse Transcriptase) is an RNA-dependent DNA polymerase requiring a DNA primer and an RNA template to synthesize a complementary DNA strand. The enzyme is a product of the pol gene of M-MLV and consists of a single subunit with a molecular weight of 71 kDa. M-MLV RT has a weaker intrinsic RNase H activity than Avian Myeloblastosis Virus (AMV) reverse transcriptase which is important for achieving long full-length complementary DNA (>7 kB).

M-MLV can be use for first strand cDNA synthesis and primer extensions. Storage is recommend at −20° C. in 20 mM Tris-HCl (pH 7.5), 0.2M NaCl, 0.1 mM EDTA, 1 mM DTT, 0.01% Nonidet® P-40 and 50% glycerol. The standard reaction conditions are 50 mM Tris-HCl (pH 8.3), 7 mM $MgCl_2$, 40 mM KCl, 10 mM DTT, 0.1 mg/ml BSA, 0.5 mM $^3H$-dTTP, 0.025 mM oligo(dT)$_{50}$ and 0.25 mM poly(A)$_{400}$ at 37° C.

M-MLV Reverse Transcriptase, RNase H Minus

This is a form of Moloney murine leukemia virus reverse transcriptase which has been genetically altered to remove the associated ribonuclease H activity (Tanese and Goff, 1988). It can be used for first strand cDNA synthesis and primer extension. Storage is typically at 20° C. in 20 mM Tris-HCl (pH 7.5), 0.2M NaCl, 0.1 mM EDTA, 1 mM DTT, 0.01% Nonidet® P-40 and 50% glycerol.

AMV Reverse Transcriptase

Avian Myeloblastosis Virus reverse transcriptase is a RNA dependent DNA polymerase that uses single-stranded RNA or DNA as a template to synthesize the complementary DNA strand (Houts et al., 1979). It has activity at high temperature (42° C.–50° C.). This polymerase has been used to synthesize long cDNA molecules.

Standard reaction conditions are 50 mM Tris-HCl (pH 8.3), 20 mM KCl, 10 mM $MgCl_2$, 500 μM of each dNTP, 5 mM dithiothreitol, 200 μg/ml oligo-dT$_{(12-18)}$, 250 μg/ml polyadenylated RNA, 6.0 pMol $^{32}P$-dCTP and 30 U enzyme in a 7 μl volume. The reaction mixture is then incubated 45 min at 42° C. Typical storage buffer is 200 mM $KPO_4$ (pH 7.4), 2 mM dithiothreitol, 0.2% Triton X-100 and 50% glycerol. AMV may be used for first strand cDNA synthesis, RNA or DNA dideoxy chain termination sequencing, and fill-ins or other DNA polymerization reactions for which Klenow polymerase is not satisfactory (Maniatis et al., 1976).

Superscript™ II RNase H

Reverse Transcriptase (U.S. Pat. No. 5,244,797, incorporated herein by reference) is purified to near homogeneity from E. coli containing the pol gene of Moloney Murine Leukemia Virus. The enzyme is used to synthesize first strand cDNA and will generally give higher yields of cDNA and more full length product than other reverse transcriptases.

An exemplary RT PCR that employs SUPERSCRIPT™ can be found in the Gibco catalog. Briefly, a 20-μl reaction volume can be used for 1–5 μg of total RNA or 50–500ng of mRNA. The following components are added to a nuclease-free microcentrifuge tube: 1 μl Oligo (dT)12–18 (500 μg/ml) 1–5 μg total RNA and sterile, distilled water is added to a final volume of 12 μl. The reaction mixture is heated to 70° C. for 10 min and quickly chilled on ice. The contents of the tube are collected by brief centrifugation. To this precipitate is added: 4 μl 5X First Strand Buffer, 2 μl 0.1 M DTT and 1 μl 10 mM dNTP Mix (10 mM each dATP, dGTP, dCTP and dTTP at neutral pH). The contents are mixed gently and incubate at 42° C. for 2 min. Then 1 μl (200 units) of Superscript II™ is added and the reaction mixture is mixed by pipetting gently up and down. This mixture is then incubated for 50 min at 42° C. and then inactivated by heating at 70° C. for 15 min. The cDNA can now be used as a template for amplification in PCR. However, amplification of some PCR targets (those >1 kb) may require the removal of RNA complementary to the cDNA. RNA complementary to the cDNA may be removed by adding 1 μl (2 units) of E. coli RNase H and incubating at 37° C. for 20 min.

Retrotherm™ RT (Epicentre technologies) is a thermostable reverse transcriptase and DNA polymerase derived from a thermophilic bacterium. This thermostable enzyme has both RNA- and DNA-dependent DNA polymerase activities under the same reaction conditions. These characteristics enable researchers to synthesize both strands of a specific cDNA in a single tube with no buffer changes. The only components needed are Retrotherm™ RT, the Retrotherm Reaction Buffer™ supplied with the enzyme, deoxynucleoside-triphosphates (dNTPs), an RNA template and specific primers for synthesis of each strand of cDNA. After first-strand synthesis, the RNA:DNA hybrid is thermally denatured to allow the second-strand primer to hybridize to the cDNA for second-strand synthesis in the same buffer. The high reaction temperatures possible with Retrotherm RT minimize secondary structure in templates. Thus, when primers are available for both strands, single-tube cDNA synthesis with Retrotherm RT is easy, fast and powerful, even when working with mixed populations of RNA. Retrotherm™ RT has no Rnase H activity.

If specific primers are available for priming synthesis of both cDNA strands from a target RNA, then single-tube cDNA synthesis with Retrotherm™ RT is fast and convenient, even when working with mixed populations of RNA. In these cases, the enzyme's thermostability and its combination of RNA- and DNA-dependent DNA polymerase activities that function well in the same buffer give Retrotherm™ RT an advantage over other reverse transcriptases.

The amount of RNA needed depends on the application and whether the sample consists of a single RNA species or a mixture of different RNAs. Similarly, the optimal enzyme concentration will vary with the amount and nature of the template. A typical 50 μl reaction contains 0.5 to 5.0 units of Retrotherm™ RT. Insufficient enzyme may fail to produce full-length product. Excess enzyme may result in failure to produce discrete bands. Two templates of the same size but differing in sequence, or different amounts of the same template, may have different optimal enzyme concentrations.

RetroAmp™

RetroAmp™ RT DNA Polymerase (Epicentre Technologies), is a highly efficient, thermally stable enzyme. The use of a thermal stable polymerase allows reverse transcription to take place at an elevated temperature, minimizing the effects of RNA secondary structure. RetroAmp™ is available in a commercial preparation with a 10X PCR Enhancer (with betaine) referred to as MasterAmp™. The presence of betaine (trimethyl glycine) in the MasterAmp™ 10X PCR Enhancer substantially improves the yield and specificity of amplification of many target sequences, especially those containing a high G+C content or secondary structure. Betaine lowers the melting temperature of G+C rich regions to a temperature more similar to A+T(U) rich regions. This results in destabilization of double-stranded regions which limits polymerase pausing, thereby increasing the yield of full-length product. In addition, betaine also may enhance PCR by protecting DNA polymerases from thermal denaturation.

Typically in the RT-PCR reaction, 50 μl reactions are assembled on ice as two separate 25 μl premixes and combined just before the reverse transcription step to minimize RNA sample degradation. One premix includes the dNTPs, primers, and the RNA template. The other premix included all other reaction components. The reactions contain 1X RT-PCR Buffer that comprises 3.0 mM $MgCl_2$, 1X MasterAmp™ PCR Enhancer, 0.5 mM $MnSO_4$, 400 μM each dNTP, 12.5 pmoles of each primer, 100 ng of total RNA template and 2.5 units of RetroAmp™ RT DNA Polymerase. Standard reactions are incubated at 60° C. for 20 minutes for first strand cDNA synthesis, followed by 30–35 cycles of PCR. Annealing temperatures vary depending on the primer pair used; typically samples are denatured at 92° C. for 30 seconds, annealed at 60° C. for 30–60 seconds, and extended at 72° C. for 60 seconds. Ten percent of each reaction (5 μl) may be separated by agarose gel electrophoresis and visualized with ethidium bromide staining.

RetroAmp™ RT DNA

Polymerase can efficiently reverse transcribe RNA into cDNA at the high temperatures for such reactions. The RetroAmp™ RT-PCR produces abundant specific products with reverse transcription temperatures up to 70° C., depending on the primer sequences and template abundance in the reaction. In the manufacture's specification the ability of RetroAmp™ RT DNA Polymerase to perform high-temperature RT-PCR, is demonstrated by performing RT-PCR using four different first-strand synthesis incubation temperatures (55° C., 60° C., 65° C., and 70° C.) with two different templates. Primers that amplify a 479 bp region of E. coli 16S rRNA were used in a standard reaction with the following cycling conditions: RNA was reverse transcribed at the specified temperature for 20 minutes, then 20 cycles of 92° C. for 30 seconds and 68° C. for 60 seconds were performed. Primers that amplify a 250 bp region of the [beta]-actin message from human placental RNA were also used in a standard reaction with the following cycling profile: RNA was reverse transcribed at the specified temperature for 20 minutes, then 35 cycles of 92° C. for 40 seconds and 70° C. for 60 seconds were performed. These high annealing temperatures were possible because of the primer sequences chosen and the optimized buffer conditions used, including the presence of MasterAmp™ PCR Enhancer. The 16S rRNA product was optimally amplified with a reverse transcription temperature of 65° C. and the [beta]-actin message amplifies well under all temperatures tested.

Thermoscript™

Thermoscript™ (Gibco-BRL) is an avian reverse transcriptase that has been shown to be useful for high temperature cDNA synthesis to improve RT-PCR (Schwabe et al., 1998). It is cloned RT in which the active site of the RNase H domain has been mutated thereby reducing the RNase H by 99.5% as compared to native AMV. Thermoscript™ is operative in the temperature range between about 50° C. and about 70° C., a description of the efficacy of the Thermoscript™ at this temperature range is given in a FIG. 2 of the product description on the manufacturer' web site at http://www2.lifetech.com/catalog/techline/molecular_biology/product_description/thrmsc rp.html. The optimized conditions for first strand synthesis by Thermoscript™ have been described by Schwabe et al., 1998. Briefly, the 20 μl reaction mixture for the synthesis contains 50 mM Tris-acetate (pH 8.4); 75 mM K-acetate; 8 mM Mg-acetate; 5 mM dithioreitol; 1 mM each of dATP, DTTP, dCTP and dGTP; 0.5 μg oligo (dT); 2.5mg RNA; 40 units RNase inhibitor and 15 units Thermoscript RT. The RT-PCR procedure, total cell RNA and oligo(dT) are incubated at 65° C. for 5 minutes and cooled on wet ice and cDNA synthesis reaction mixture is added. The reaction tubes are transferred to a prewarmed heating block and incubated for 50 minutes. Following RT inactivation, RNA is degraded by an RNase H. For PCR 20 μl cDNA reaction mixture is added to a 50 μl PCR mixture and incubated for 2 minutes at 94° C. PCR conditions involved 35 cycles of 94° C. for 30s, 55–60° C. for 30s and 68–72° C. for 1 to 15 minutes. Exemplary polymerases used for this method were Platinum Taq™ and eLONGase®.

rTth Reverse Transcriptase

The GeneAmp Thermostable rTth Reverse Transcriptase (Perkin-Elmer) catalyses the reverse transcription of RNA to cDNA at elevated temperature (60–70° C.) and subsequently amplifies cDNA using the same recombinant thermostable enzyme—rTth DNA Polymerase. The procedure begins with first strand cDNA synthesis from RNA, with rTth DNA Polymerase acting as a reverse transcriptase in the presence of $MnCl_2$ (Myers and Gelfand, 1991; Young et al., 1993).

Subsequently, in the presence of MgCl$_2$, Chelating Buffer and the second primer, synthesis of second strand cDNA and amplification of cDNA is initiated.

The ability of thermostable rTth DNA Polymerase to efficiently reverse transcribe RNA templates at 70° C. is useful in the present invention because the secondary structures are unstable at the higher reaction temperatures. An additional advantage of performing reverse transcription at higher temperatures is increased specificity of primer hybridization and subsequent extension by the rTth DNA Polymerase and therefore sensitivity of the reaction.

Reverse transcription using rTth DNA Polymerase is accomplished using a single specific oligonucleotide primer complementary to the 3'-terminus of the RNA. Subsequent PCR amplifications are achieved using specific oligonucleotide primer pairs at intervals progressively 3' to the resultant first-strand cDNA. The reverse transcription is performed at 60° C. for 2 hours, followed by a 1 minute predenaturation step at 95° C. then 40 cycles of 95° C. for 15s and 65° C. for 30s, for each primer pair. Starting template can be a poly(A) RNA or RNA from a given tissue with a target copy number of approximately 10$^8$ copies. The tissue RNA can be isolated from any desired tissues by techniques well known to those of skill in the art and also by techniques described elsewhere is the specification.

Having produced the first strand of the cDNA species using reverse transcription, the present invention also contemplates the use of various DNA polymerases, either described herein or known to those of ordinary skill in the art, to produce the second strand of the double-stranded cDNA moiety. Exemplary, but not limiting, polymerases are described below.

Bst DNA Polymerase Large Fragment

Bst DNA Polymerase Large Fragment is the portion of the Bacillus stearothermophilus DNA Polymerase protein that contains the 5'→3' polymerase activity, but lacks the 5'→3' exonuclease domain. BST Polymerase Large Fragment is prepared from an *E. coli* strain containing a genetic fusion of the *Bacillus stearothermophilus* DNA Polymerase gene, lacking the 5'→3' exonuclease domain, and the gene coding for *E. coli* maltose binding protein (MBP). The fusion protein is purified to near homogeneity and the MBP portion is cleaved off in vitro. The remaining polymerase is purified free of MBP (Iiyy et al., 1991).

Bst DNA polymerase can be used in DNA sequencing through high GC regions (Hugh and Griffin, 1994; McClary et al., 1991) and rapid sequencing from nanogram amounts of DNA template (Mead et al., 1991). The reaction buffer is 1X ThermoPol Buffer [20 mM Tris-HCl (pH 8.8 at 25° C.), 10 mM KCl, 10 mM (NH$_4$)$_2$SO$_4$, 2 mM MgSO$_4$, 0.1% Triton X-100], typically supplied with enzyme as a 10X concentrated stock.

Bst DNA Polymerase does not exhibit 3'→5' exonuclease activity. 100 μ/ml BSA or 0.1% Triton X- 100 is required for long term storage. Reaction temperatures above 70° C. are not recommended. Heat inactivated by incubation at 80° C. for 10 min. Bst DNA Polymerase cannot be used for thermal cycle sequencing. Unit assay conditions are 50 mM KCl, 20 mM Tris-HCl (pH 8.8), 10 mM MgCl$_2$, 30 nM M13mp18 ssDNA, 70 nM M13 sequencing primer (–47) 24 mer, 200 μM daTP, 200 μM dCTP, 200 μM dGTP, 100 μM $^3$H-dTTP, 100 μg/ml BSA and enzyme. Incubate at 65° C. Storage buffer is 50 mM KCl, 10 mM Tris-HCl (pH 7.5), 1 mM dithiothreitol, 0.1 mM EDTA, 0.1% Triton-X-100 and 50% glycerol. Storage is at –20° C.

VENT$_R$®DNA Polymerase and VENT$_R$® (exo-) DNA Polymerase

VENT$_R$® DNA Polymerase is a high-fidelity thermophilic DNA polymerase. The fidelity of VENT$_R$® DNA Polymerase is 5–15-fold higher than that observed for Taq DNA Polymerase (Mattila et al., 1991; Eckert and Kunkel, 1991). This high fidelity derives in part from an integral 3'→5' proofreading exonuclease activity in VENT$_R$® DNA Polymerase (Mattila et al., 1991; Kong et al., 1993). Greater than 90% of the polymerase activity remains following a 1 h incubation at 95° C.

VENT$_R$® (exo-) DNA Polymerase has been genetically engineered to eliminate the 3'→5' proofreading exonuclease activity associated with VENT$_R$® DNA Polymerase (Kong et al., 1993). This is the preferred form for high-temperature dideoxy sequencing reactions and for high yield primer extension reactions. The fidelity of polymerization by this form is reduced to a level about 2-fold higher than that of Taq DNA Polymerase (Mattila et al., 1991; Eckert and Kunkel, 1991). VENT$_R$® (exo-) DNA Polymerase may be used for DNA sequencing.

Both VENT$_R$® and VENT$_R$® (exo-) are purified from strains of *E. coli* that carry the Vent DNA Polymerase gene from the archaea *Thermococcus litoralis* (Perler et al., 1992). The native organism is capable of growth at up to 98° C. and was isolated from a submarine thermal vent (Belkin and Jannasch, 1985). They are useful in primer extension, thermal cycle sequencing and high temperature dideoxy-sequencing.

DEEP VENT$_R$™ DNA Polymerase and DEEP VENT$_R$™(exo-) DNA Polymerase

DEEP VENT$_R$™ DNA Polymerase is the second high-fidelity thermophilic DNA polymerase available from New England Biolabs. The fidelity of DEEP VENT$_R$™ DNA Polymerase is derived in part from an integral 3'→5' proofreading exonuclease activity. DEEP VENT$_R$™ is even more stable than VENT$_R$™ at temperatures of 95° C. to 100° C.

DEEP VENT$_R$™ (exo-) DNA Polymerase has been genetically engineered to eliminate the 3'→5' proofreading exonuclease activity associated with DEEP VENT$_R$™ DNA Polymerase. This exo- version can be used for DNA sequencing but requires different dNTP/ddNTP ratios than those used with VENT$_R$™(exo-) DNA Polymerase. Both DEEP VENT$_R$™ and DEEP VENT$_R$™ (exo-) are purified from a strain of *E. coli* that carries the DEEP VENT$_R$™ DNA Polymerase gene from Pyrococcus species GB-D (Perler et al., 1996). The native organism was isolated from a submarine thermal vent at 2010 meters (Jannasch et al., 1992) and is able to grow at temperatures as high as 104° C. Both enzymes can be used in primer extension, thermal cycle sequencing and high temperature dideoxy-sequencing.

T7 DNA Polymerase (unmodified)

T7 DNA polymerase catalyzes the replication of T7 phage DNA during infection. The protein dimer has two catalytic activities: DNA polymerase activity and strong 3'→5' exonuclease (Hori et al., 1979; Engler et al., 1983; Nordstrom et al., 1981). The high fidelity and rapid extension rate of the enzyme make it particularly useful in copying long stretches of DNA template.

T7 DNA Polymerase consists of two subunits: T7 gene 5 protein (84 kilodaltons) and *E. coli* thioredoxin (12 kilodaltons) (Hori et al., 1979; Studier et al., 1990; Grippo and Richardson, 1971; Modrich and Richardson, 1975;

Adler and Modrich, 1979). Each protein is cloned and overexpressed in a T7 expression system in *E. coli* (Studier et al., 1990). It can be used in second strand synthesis in site-directed mutagenesis protocols (Bebenek and Kunkel, 1989).

The reaction buffer is 1X T7 DNA Polymerase Buffer [20 mM Tris-HCl (pH 7.5), 10 mM $MgCl_2$ and 1 mM dithiothreitol]. Supplement with 0.05 mg/ml BSA and dNTPs. Incubate at 37° C. The high polymerization rate of the enzyme makes long incubations unnecessary. T7 DNA Polymerase is not suitable for DNA sequencing.

Unit assay conditions are 20 mM Tris-HCl (pH 7.5), 10 mM $MgCl_2$, 1 mM dithiothreitol, 0.05 mg/ml BSA, 0.15 mM each dNTP, 0.5 mM heat denatured calf thymus DNA and enzyme. Storage conditions are 50 mM $KPO_4$ (pH 7.0), 0.1 mM EDTA, 1 mM dithiothreitol and 50% glycerol. Store at −20° C.

DNA Polymerase I (*E. coli*)

DNA Polymerase I is a DNA-dependent DNA polymerase with inherent 3'→5' and 5'→3' exonuclease activities. The 5'→3' exonuclease activity removes nucleotides ahead of the growing DNA chain, allowing nick-translation. It is isolated from *E. coli* CM 5199, a lysogen carrying λpolA transducing phage (Murray and Kelley, 1979). The phage in this strain was derived from the original polA phage encoding wild-type Polymerase I.

Applications include nick translation of DNA to obtain probes with a high specific activity (Meinkoth and Wahl, 1987) and second strand synthesis of cDNA (Gubler and Hoffmann, 1983; D'Alessio and Gerard, 1988). The reaction buffer is *E. coli* Polymerase I/Klenow Buffer [10 mM Tris-HCl (pH 7.5), 5 mM $MgCl_2$ and 7.5 mM dithiothreitol]. Supplement with dNTPs.

DNase I is typically not included with this enzyme and must be added for nick translation reactions. Heat inactivation is for 20 min at 75° C. Unit assay conditions are 40 mM $KPO_4$ (pH 7.5), 6.6 mM $MgCl_2$, 1 mM 2-mercaptoethanol, 20 μM dAT copolymer, 33 μM dATP and 33 μM $^3$H-dTTP. Storage conditions are 0.1 M $KPO_4$ (pH 6.5), 1 mM dithiothreitol and 50% glycerol. Store at −20° C.

DNA Polymerase I, Large (Klenow) Fragment

Klenow fragment is a proteolytic product of *E. coli* DNA Polymerase I which retains polymerization and 3'→5' exonuclease activity, but has lost 5'→3' exonuclease activity. Klenow retains the polymerization fidelity of the holoenzyme without degrading 5' termini.

A genetic fusion of the *E. coli* polA gene, that has its 5'→3' exonuclease domain genetically replaced by maltose binding protein (MBP). Klenow Fragment is cleaved from the fusion and purified away from MBP. The resulting Klenow fragment has the identical amino and carboxy termini as the conventionally prepared Klenow fragment.

Applications include DNA sequencing by the Sanger dideoxy method (Sanger et al., 1977), fill-in of 3' recessed ends (Sambrook et al., 1989), second-strand cDNA synthesis, random priming labeling and second strand synthesis in mutagenesis protocols (Gubler, 1987)

Reactions conditions are 1X *E. coli* Polymerase I/Klenow Buffer (10 mM Tris-HCl (pH 7.5), 5 mM MgCl2, 7.5 mM dithiothreitol). Supplement with dNTPs. Klenow fragment is also 50% active in all four standard NEBuffers when supplemented with dNTPs. Klenow may be heat inactivated by incubating at 75° C. for 20 min. Fill-in conditions: DNA should be dissolved, at a concentration of 50 μg/ml, in one of the four standard NEBuffers (1X) supplemented with 33 μM each dNTP. Add 1 unit Klenow per μg DNA and incubate 15 min at 25° C. Stop reaction by adding EDTA to 10 mM final concentration and heating at 75° C. for 10 min. Unit assay conditions 40 mM KPO4 (pH 7.5), 6.6 mM MgCl2, 1 mM 2-mercaptoethanol, 20 μM dAT copolymer, 33 μM dATP and 33 μM $^3$H-dTTP. Storage conditions are 0.1 M $KPO_4$ (pH 6.5), 1 mM dithiothreitol, and 50% glycerol. Store at −20° C.

Klenow Fragment (3'→5' exo-)

Klenow Fragment (3'→5' exo-) is a proteolytic product of DNA Polymerase I which retains polymerase activity, but has a mutation which abolishes the 3'→5' exonuclease activity and has lost the 5'→3' exonuclease (Derbyshire et al., 1988). It is a genetic fusion of the *E. coli* polA gene that has its 3'→5' exonuclease domain genetically altered and 5'→3' exonuclease domain replaced by maltose binding protein (MBP). Klenow Fragment exo- is cleaved from the fusion and purified away from MBP. Applications include random priming labeling, DNA sequence by Sanger dideoxy method (Sanger et al., 1977), second strand cDNA synthesis and second strand synthesis in mutagenesis protocols (Gubler, 1987).

Reaction buffer is 1X *E. coil* Polymerase I/Klenow Buffer [10 mM Tris-HCl (pH 7.5), 5 mM $MgCl_2$ and 7.5 mM dithiothreitol]. The reaction mixture is supplemented with dNTPs. Klenow Fragment exo- is also 50% active in all four standard NEBuffers when supplemented with dNTPs. Klenow Fragment exo- may be heat inactivated by incubating at 75° C. for 20 min. When using Klenow Fragment (3'→5' exo-) for sequencing DNA using the dideoxy method of Sanger et al. (1977), an enzyme concentration of 1 unit/5 μl is recommended.

Unit assay conditions are 40 mM $KPO_4$ (pH 7.5), 6.6 mM $MgCl_2$, 1 mM 2-mercaptoethanol, 20 μM dAT copolymer, 33 μM dATP and 33 μM $^3$H-dTTP. Storage conditions are 0.1 M $KPO_4$ (pH 7.5), 1 mM dithiothreitol and 50% glycerol. Store at −20° C.

T4 DNA Polymerase

T4 DNA Polymerase catalyzes the synthesis of DNA in the 5'→3' direction and requires the presence of template and primer. This enzyme has a 3'→5' exonuclease activity which is much more active than that found in DNA Polymerase I. Unlike *E. coli* DNA Polymerase I, T4 DNA Polymerase does not have a 5'→3' exonuclease function.

T4 DNA Polymerase is purified from a strain of *E. coli* that carries a T4 DNA Polymerase overproducing plasmid. Applications include removing 3' overhangs to form blunt ends (Tabor and Struhl, 1989; Sambrook et al., 1989), 5' overhang fill-in to form blunt ends (Tabor and Struhl, 1989; Sambrook et al., 1989), single strand deletion subcloning (Dale et al., 1985), second strand synthesis in site-directed mutagenesis (Kunkel et al., 1987), and probe labeling using replacement synthesis (Tabor and Struhl, 1989; Sambrook et al., 1989).

The reaction buffer is 1X T4 DNA Polymerase Buffer [50 mM NaCl, 10 mM Tris-HCl, 10 mM $MgCl_2$ and 1 mM dithiothreitol (pH 7.9 at 25° C.)]. Supplement with 40 μg/ml BSA and dNTPs, which are typically not included in supplied 10X buffer. The reaction temperature varies for the protocol being used, but such conditions are known to those of skill in the art (Tabor and Struhl, 1989; Sambrook et al., 1989).

It is recommended to use 100 μM of each dNTP, 1–3 units polymerase/μg DNA and incubation at 12° C. for 20 min in the above reaction buffer (Tabor and Struhl, 1989; Sambrook et al., 1989). T4 DNA Polymerase may be heat inactivated by incubating at 75° C. for 10 min. T4 DNA Polymerase is active in all four standard NEBuffers when supplemented with dNTPs.

Unit assay conditions are 50 mM NaCl, 10 mM Tris-HCl, 10 mM $MgCl_2$, 1 mM dithiothreitol (pH 7.9 at 25° C.), 33 μM dATP, dCTP and dGTP, 33 μM $^3$H dTTP, 70 μg/ml denatured calf thymus DNA, and 170 μg/ml BSA. These reaction conditions differ from those used in the Reaction Buffer. Storage conditions are 100 mM $KPO_4$ (pH 6.5), 10 mM 2-mercaptoethanol and 50% glycerol. Store at −20° C.

Taq Polymerases

Native Taq™ (Perkin-Elmer) DNA Polymerase is a thermostable, 94-kDa DNA polymerase isolated from *Thermus aquaticus* YT1. It is primarily used for exact replication of studies performed prior to the availability of recombinant AmpliTaq DNA Polymerase. AmpliTaq DNA Polymerase is a 94-kDa, gelatin-free, thermostable, recombinant DNA polymerase obtained by expression of a modified form of the Taq DNA Polymerase gene cloned in *E. coli* (Lawyer et al., 1989; Lawyer et al., 1993).

The thermal activity profile of AmpliTaq DNA Polymerase is ideal for PCR applications because its optimal activity is in the same range at which stringent annealing of primers occurs (55° C.–75° C.). The enzyme's PCR cycling half-life is 50 cycles at 95° C., providing sufficient thermostability such that there is no substantial loss of enzymatic activity, even after repeated exposure to the highest temperatures recommended in most PCR protocols. The enzyme has a 5'→3' exonuclease activity which has been exploited in development of a homogeneous simultaneous signal generation assay (Holland et al., 1991) and it lacks 3'→5' exonuclease activity.

Tfl DNA Polymerase

Tfl is yet another polymerase enzyme with an apparent molecular weight of approximately 94 kDa. It was isolated from *Thermus flavus* (Kaledin et al., 1981). The isolated enzyme is thermostable and has a temperature optimum on the DNA templates at 70° degrees and that on RNA templates at 50 degrees. The enzyme does not appear to contain contaminant endo- and exonuclease activities. For maximal activity, the enzyme requires the presence of template, four deoxyribonucleoside triphosphates and monovalent and bivalent cations in the incubation mixture. The enzyme is highly active when "activated" DNA, poly(dA)-poly(dT), poly(dA)-oligo(dT) 10 and poly(rA)-oligo(dT)10 are used as templates, moderately active on single-stranded and double-stranded DNAs and inactive on poly(rC)-oligo(dG) 12–18 and native RNA molecules. Tfl is commercially available from a variety of sources including Promega.

Tht DNA Polymerase was isolated from *Thermus thermophilus* HB-8 (Ruttimann et al., 1985). This enzyme catalyzes the DNA polymerization, of nucleotides into duplex DNA in the 5'→3' direction in the presence of $MgCl_2$. Also the enzyme catalyzes RNA polymerization in the presence of $MgCl_2$. The ability of Tth DNA polymerase to act as an RT at elevated temperatures is particularly useful in the context of the present invention.

Tli DNA Polymerase

Tli DNA polymerase is an extremely thermostable polymerase that replicates DNA at 75° C. and remains functional even after incubation at 100° C. Tli DNA polymerase has an integral 3'→5" exonuclease activity (proofreading) function. The enzyme has a molecular weight of approximately 90 kDa (Mattila et al., 1991) and is commercially available from a variety of sources.

UlTma™ DNA Polymerase

Is a thermostable DNA polymerase specifically designed, thoroughly optimized and tested for its ability to repair 3'-mismatches in PCR amplification, to provide high yield of specific PCR product, and to produce blunt-ended PCR products suitable for cloning and gene expression. Ultma™ DNA Polymerase, a 70-kDa recombinant enzyme, is encoded by a modified form of a *Thermotoga maritima* DNA polymerase gene which has been cloned and expressed in *E. coli* (U.S. Pat. No. 5,310,652, incorporated herein by reference). The enzyme has been specifically engineered to achieve an optimal balance between polymerase and proofreading activity. It has also been optimized for higher yield by using a hot start reaction.

6. Separation Methods

It normally is desirable, at one stage or another, to separate the amplification products from reagents, such as the template or excess primers, or from other amplification products. In one embodiment, amplification products are separated by agarose, agarose-acrylamide or polyacrylamide gel electrophoresis using standard methods. See Sambrook et al., 1989. When working with nucleic acids, denaturing PAGE is preferred.

7. Blotting Methods

In certain embodiments, blotting techniques will be used to examine the size of cDNAs made or to verify the completion of a PCR reaction. Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting of RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will bind a portion of the target sequence under renaturing conditions. Unbound probe is then removed, and detection is accomplished as described above.

8. Kits

All the essential materials and reagents required for performing the methylation specific PCR method of the present invention may be assembled together in a kit. Such kits generally will comprise preselected primers and may include other oligo- and polynucleotides, such as probes and expression vectors. Also included may be enzymes suitable for amplifying nucleic acids including various polymerases (reverse transcriptases, polymerase, etc.), dNTPs and buffers to provide the necessary reaction mixture for amplification. Such kits also generally will comprise, in suitable means, distinct containers for each individual primer, probe, vector, dNTPs, buffer and enzyme(s).

9. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Methods

DNA was extracted from 3–5 ml of blood using the Puregene kit (Gentra systems). 1 μg of DNA was subjected to bisulfite treatment as described (Clark et al., 1994; Herman et al., 1996) using the modifications described in Kubota et al., 1997. PCR was carried out in a 50 μl volume containing 1 X PCR buffer II (Perkin-Elmer), 4.5 mM MgCl$_2$, 200 μM dNTPs, 0.5 μM NM-BS primers, 1.0–1.5 μM FX-BS primers (sequences in table 1), 1 unit of Amplitaq Gold enzyme (Perkin-Elmer) and approximately 30 ng of bisulfite-modified DNA. The polymerase was activated at 95° C. for 10 mins, and DNA amplified in a Perkin-Elmer model 9600 thermocycler for 35 cycles at 94° C. for 30s, 64° C. for 30s and 72° C. for 30s, followed by a final extension at 72° C. for 10 mins. Negative controls using untreated DNA and no DNA were also performed.

For non-radioactive amplification across the triplet repeat, modifications of the protocol by Papp et al., 1996 were carried out as follows: 400 ng of DNA was used for digestion with HindIII restriction enzyme. Reactions were set up in a 6 μvolume and incubated for 3 hours at 37° C. The digested DNA was subjected to PCR using primers that flank the triplet repeat, FXF-1 (nt. pos. 13708, 5'-AGGCGCTCAGCTCCGTTTCG-3' SEQ ID NO:10) and FXR-1 (nt. pos. 13922, 5'-AGAGGTGGGCTGCGGGCGCT-3'SEQ ID NO:11). Nucleotide positions are based on the numbering of Verkerk et al., 1991 (Genbank accession no. L29074). PCR was carried out in a 50 μl volume containing 1 X PCR buffer II (Perkin-Elmer), 2.5 mM MgCl$_2$, 200 μM dNTPs, 0.4 μM of each primer, 1 unit of Amplitaq Gold enzyme and 2.5M betaine. A negative control using no DNA was performed. PCR products were visualized by electrophoresis of 10 μl of reaction on a 2.7% agarose gel, stained with ethidium bromide, under UV illumination.

EXAMPLE 2

Sodium Bisulfite Treatment of FMR1 DNA

Figure 1A:

Methylation studies of the 5' untranslated region of the FMR1 gene have shown that CpG sites within and around the triplet repeat are methylated in fragile X individuals and are unmethylated in normal and premutation individuals (Hansen et al., 1992; Homstra et al., 1993). Sodium bisulfite treatment of DNA, which converts unmethylated cytosine to uracil, therefore results in a changed 5' untranslated FMR-1 sequence in affected individuals compared to normal and premutation individuals (FIG. 1). PCR primers were designed that were specific for the antisense strand of the methylated and unmethylated versions of the FMR-1 gene and that were also specific for the treated version of the gene (FIG. 1 and Table 1).

TABLE 1

Primers Used for Methylation-Specific PCR

| Primers | Sequence (5'→3') | Size (bp) | cDNA position | SEQ ID NO |
|---------|------------------|-----------|---------------|-----------|
| FX-BS-for | ACCGATTCCCAACAACGCGCATA | 255 | 13551 | 12 |
| FX-BS-rev | TTTCGTTATCGTCGTCGTTCGC | | 13803 | 13 |
| NM-BS-for | ACACACATACACACACTCCCAAA | 163 | 13565 | 14 |
| NM-BS-rev | TTGAAATGGAGTTGAGTGTTTGAT | | 13728 | 15 |

The FX-BS primers are specific for the methylated version of FMR-1 gene and the NM-BS primers for the unmethylated versions. Sequence differences between primers designed to the treated DNA strand and the untreated DNA strand are in bold and italics. Differences between the methylated and unmethylated sequences are underlined. cDNA position is the location of the 5' nucleotide of the primer according to the numbering of Verkerk et al., 1991 (Genbank Accession No. L29074).

DNA samples of full mutation, premutation and normal male individuals (mutation status previously determined by Southern blot analysis) were treated with sodium bisulfite and amplified with primers specific for the methylated sequence (FX primers) and unmethylated sequence (NM primers) in a duplex PCR reaction. A 163 bp amplification product specific for the unmethylated sequence (NM-specific) was observed in normal and premutation individuals. A 255 bp amplification product specific for the methylated sequence (FX-specific) was observed in individuals who carried a full mutation, and in individuals mosaic for a full mutation. The 163 bp NM-specific amplification product was additionally observed in some cases. No amplification was observed with untreated DNA. Normal and premutation males could be distinguished by amplification across the triplet repeat using conventional PCR (as described in Example 1). Individuals with repeat lengths in the normal range (5–50 repeats) showed amplification products of between 169–304 bps, whereas individuals with repeat lengths in the premutation range (50–200 repeats) did not show any amplification.

EXAMPLE 3

Retrospective Diagnostic Study

A retrospective blinded study was performed on 100 DNA samples previously analyzed by Southern blot. These samples were obtained from 52 normal, 31 full mutation, 10 premutation, 6 premutation/full mutation mosaic and 1 normal/full mutation mosaic male individuals. The results of the methylation PCR assay corresponded with the Southern blot results.

All normal and premutation individuals showed NM-specific amplification only. 29 individuals with full mutations showed FX-specific amplification with some also showing NM-specific amplification, while 2 individuals showed NM-specific amplification only. Investigation of these 2 patients showed that both had borderline premutation/full mutation and demonstrated less than 10% methylation by Southern blot analysis. All 7 individuals mosaic for full mutations showed both FX- and NM-specific amplification. Amplification across the triplet repeat by conventional PCR was performed for all the individuals and used to distinguish between normal and premutation carriers. All 52 normal individuals presented with an amplification product, while the premutation, full mutation and mosaic individuals did not produce any amplification. By this criteria, the two patients with borderline premutation/full mutation expansions who did not show FX-specific amplification, were classified as premutation carriers.

Additional patients were analyzed to further test the sensitivity of methylation-specific PCR in the presence of mosaicism. 5 fragile X patients mosaic for the full mutation and 4 patients with full mutations mosaic for methylation were analyzed. FX-specific amplification product was observed in all cases. In addition, mosaicism for methylation was also present in a number of individuals included in the blinded study. For example, 2 of the full mutations and 3 of the premutation/full mutations were mosaic for methylation. FX-specific amplification was observed for all these cases.

EXAMPLE 4

Prospective Diagnostic Study

A prospective study also was undertaken on 30 male blood samples referred for diagnosis of fragile X. Methylation-specific PCR showed the presence of methylation in two cases and no amplification across the triplet repeat by conventional PCR, consistent with a full mutation and therefore positive for fragile X. An absence of methylation was observed in the remaining 28 cases with a corresponding normal size triplet repeat amplification product, indicative of normal for fragile X. These results corresponded to those obtained by Southern blot analysis performed in parallel and demonstrate that the methylation-specific PCR described in the present invention may be used as a fast reliable diagnostic tool for identifying males with fragile X syndrome.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the [compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adler and Modrich, *J. Biol. Chem.*, 254: 11605–11614, 1979.
An et al., *J Clin Microbiol*;33(4): 860–867 1995.
Beaucage, and Lyer, *Tetrahedron*, 48: 2223–2311, 1992
Bebenek and Kunkel, *Nucl. Acids Res.*, 17: 5408, 1989.
Belkin and Jannasch, *Arch. Microbiol.*, 141: 181–186, 1985.
Bell et al., *Cell* 64 861–66, 1991.
Bellus, *J. Macromol. Sci. Pure Appl. Chem.*, A31(1): 1355–1376, 1994.
Brown, *Am. J. Human Genet.* 47 175–80, 1990.
Chen et al., *Mol. Med.* 1(2): 153–160, 1995.
Chomczynski and Sacchi, *Anal Biochem.* 162(1): 156–159, 1987.
Clark et al., *Nuc. Acids Res.* 22, 2990–2997, 1994.
D'Alessio and Gerard, *Nucl. Acids Res.*, 16: 1999–2014, 1988.
Dale et al., *Plasmid*, 13: 31–40, 1985.
Derbyshire et al., *Science*, 240(4849): 199–201, 1988.
Donahue et al., *J. Biol. Chem.* 269: 8604–8609, 1994.
Eckert and Kunkel, *PCR Methods and Applications*, 1: 17–24, 1991.
Eichler et al., *Hum. Mol. Genet.* 2(8): 1147–53, 1993.
Engler et al., *J. Biol. Chem.*, 258: 11165–11173, 1983.
Freifelder, *Physical Biochemistry Applications to Biochemistry and Molecular Biology*, 2nd ed. Wm. Freeman and Co., New York, N.Y., 1982.
Frohman, In: PCR PROTOCOLS: A GUIDE TO METHODS AND APPLICATIONS, Academic Press, N.Y., 1990.
Frommer et al., *Proc. Natl. Acad. Sci. USA* 89, 1827–1831, 1992.
Fu et al., *Cell* 67, 1047–1058, 1991.
Gillam et al., *J. Biol. Chem.* 253, 2532, 1978.
Gillam et al., *Nucleic Acids Res.* 6, 2973, 1979.
Gingeras et al., PCT Application WO 88/10315.
Grippo and Richardson, *J. Biol. Chem.*, 246: 6867–6873, 1971.
Gubler and Hoffmann, *Gene*, 25: 263–269, 1983.
Gubler, *Methods Enzymol.*, 152: 330–335, 1987.
Haddad et al., *Hum. Genet.* 97, 808–812, 1996.
Hagerman and Silverman, *Pediatrics*, 89(3): 395–400, 1992.
Hansen et al., *Hum. Mol. Genet.* 1, 571–578, 1992.
Herman et al., *Proc. Natl. Acad. Sci. USA* 93, 9821–9826, 1996.
Hirst et al., *Am. J. Hum. Genet.* 56(1): 67–74, 1995.
Holland, P., et al., *Proc. Natl. Acad. Sci. USA* 88: 7276–7280, 1991.
Hori et al., *J. Biol. Chem.*, 254: 11598–11604, 1979.
Hornstra et al., *Hum. Mol. Genet.* 2, 1659–1665, 1993.
Houts et al., *J. Virol.*, 29: 517–522, 1979.
Iiyy et al., *Biotechnique* 11: 464, 1991.
Innis et al., *PCR™ Protocols*, Academic Press, Inc., San Diego Calif., 1990.
Itakura and Riggs, *Science* 209: 1401–1405, 1980.
Itakura et al., *J. Biol. Chem.* 250, 4592 1975.
Jannasch et al., *Applied Environ. Microbiol.*, 58: 3472–3481, 1992.
Kaledin et al., *Biokhimiia.* 46(9): 1576–1584, 1981.
Khorana, *Science* 203, 614, 1979.
Kong et al., *J. Biol. Chem.*, 268: 1965–1975, 1993.
Kremer et al., *Science* 252 1711–14, 1991.
Kubota et al., *Nature Genet.* 16, 16–17, 1997.
Kunkel et al., *Methods Enzymol.*, 154: 367–382, 1987.
Kwoh et al., *Proc. Nat. Acad. Sci. USA*, 86: 1173, 1989.
Larsen et al., *Human Genetics* 100, 564–568 1997.
Lawyer, et al., *J. Biol. Chem.* 264: 6427–6437, 1989.
Lawyer, et al., *PCR Meth. and Appl.* 2(4): 275–287, 1993.
Liang and Pardee, *Science*, 257: 967–970, 1992.
Maniatis et al., *Cell*, 8: 163, 1976.
Mattila et al., *NAR*, 19: 4967–4973, 1991.
Meinkoth and Wahl, *Methods Enzymol.*, 152: 91–94, 1987.
Modrich and Richardson, *J. Biol. Chem.*, 250: 5515–5522, 1975.

Mok et al., *Gynecol Oncol.* 52(2): 247–252, 1994.
Morton et al., *J. Med. Genet.* 34, 1–5, 1997.
Mulvihill In: Ingall J R F, Mastromarino A J, eds. Prevention of hereditary large bowel cancer. New York: Alan R. Liss,: 61–75, 1983.
Murray and Kelley, *Molec. Gen. Genet.*, 175: 77–87, 1979.
Myers, T. W. and Gelfand, D. H. *Biochemistry* 30: 7661–7666, 1991.
Nordstrom et al., *J. Biol. Chem.*, 256: 3112–3117, 1981.
Oberle et al., *Science* 252, 1097–1102, 1991.
Papp et al., *Molecular diagnosis* 1, 59–64, 1996.
Pergolizzi et al., *Lancet* 339, 217–218.
Perler et al., *Adv. Protein Chem.* 48: 377–435, 1996.
Perler et al., *Proc. Nat'l Acad. Sci. USA*, 89: 5577, 1992.
Pieretti et al., *Cell* 66 1–20, 1991.
Razin and Cedar, *Microbiol Rev.*, 55(3): 451–8, 1991.
Richards et al., *J Med Genet.* 28(12): 81 8–23, 1991.
Rousseau et al., *N. Engl. J. Med.* 325, 1673–1681, 1991, 1992.
Ruttimann et al., *Eur J Biochem.* 149(1): 41–46, 1985.
Sager et al., *FASEB J.* 7(10): 964–970, 1993.
Sambrook et al., In: *Molecular Cloning: A Laboratory Manual*, second edition, Cold Spring Harbor Laboratory, Cold Spring Harbor, N.Y., 1989.
Sanger et al., *Proc. Nat'l Acad. Sci. USA*, 74: 5463–5467, 1977.
Schwabe et al., *Focus*, 20: 30–33, 1998.
Singer-Sam et al., *Mol. Cell. Biol.*, 10, 4987–4989, 1990
Stoger et al., *Cell* 73(1): 61–71, 1993.
Studier et al., *Methods Enzymol.*, 185: 60–89, 1990.
Sutcliffe et al., *Hum. Mol. Genet.* 1, 397–400, 1992.
Tabor and Struhl, In: *Current Protocols in Molecular Biology*, Ausubel et al. (Eds.), John Wiley and Sons, N.Y., pp 3.5.10–3.5.12, 1989.
Tanese and Goff, *Proc. Nat'l Acad. Sci. USA*, 85: 1977, 1988.
U.S. Pat. No. 4,704,362
U.S. Pat. No. 5,221,619
U.S. Pat. No. 5,583,013
U.S. Pat. No. 4,659,774
U.S. Pat. No. 4,683,195
U.S. Pat. No. 4,683,202
U.S. Pat. No. 4,800,159
U.S. Pat. No. 4,816,571
U.S. Pat. No. 4,883,750
U.S. Pat. No. 4,959,463
U.S. Pat. No. 5,141,813
U.S. Pat. No. 5,244,797
U.S. Pat. No. 5,262,311
U.S. Pat. No. 5,264,566
U.S. Pat. No. 5,310,652
U.S. Pat. No. 5,428,148
U.S. Pat. No. 5,554,744
U.S. Pat. No. 5,574,146
U.S. Pat. No. 5,602,244
U.S. Pat. No. 5,658,764
Verkerk et al., *Cell* 65 905–14, 1991.
Walker et al., *Proc. Nat'l Acad. Sci. USA*, 89: 392–396 1992.
Wang et al., *Nucleic Acids Res.* 8(20): 4777–90, 1980.
Warren and Nelson, *JAMA*. 16;271(7): 536–42, 1994.
Watson et al., *Cancer Res.* 54(17): 4598–4602, 1994.
Welsh et al. *Nucleic Acids Res.* 20(19): 4965–4970, 1992.
Willemsen et al. *Lancet* 345, 1147–1148, 1995.
Wu et al., *Genomics*, 4: 560, 1989.
Young, K., et al., *J. of Clinical Microbiology* 31 4: 882–886 1993.

What is claimed is:

1. A method for determining the methylation state of an FMR1 gene promoter of a male subject comprising the steps of:
   (a) denaturing a DNA sample from said subject;
   (b) subjecting the denatured DNA to bisulfite modification;
   (c) amplifying said DNA using primers pairs having the sequences
      ACCGATTCCCAACAACGCGCATA (SEQ ID NO:12) and
      TTTCGTTATCGTCGTCGTTCGC (SEQ ID NO:13), and
      ACACACATACACACACTCCCAAA (SEQ ID NO:14) and
      TTGAAATGGAGTTGAGTGTTTGAT (SEQ ID NO:15); and
   (d) detecting amplification products from step (c).

2. The method of claim 1, further comprising the step, before step (a), of obtaining a DNA sample from said subject.

3. The method of claim 2, wherein said sample is blood, amniotic fluid, buccal smears.

4. The method of claim 1, wherein denaturing comprises treatment with NaOH and heat.

5. The method of claim 1, wherein bisulfite modification comprises treatment with hydroquinone and sodium bisulfite, followed by treatment with NaOH.

6. The method of claim 1, further comprising the step of purifying said bisulfite modified DNA.

7. The method of claim 1, wherein amplification comprises PCR.

8. The method of claim 7, wherein said PCR comprises 35 cycles at 94° C. for 30 seconds, 64° C. for 30 seconds and 72° C. for 30 seconds, followed by a final extension at 72° C. for 10 minutes.

9. The method of claim 1, wherein said amplification products are unlabeled.

10. The method claim 1, wherein said amplification products are labeled with a detectable label.

11. The method of claim 10, wherein said label is radioactive, fluorescent, chemilluminescent or colorimetric.

12. The method of claim 1, wherein said detection comprises gel electrophoresis and visualization of size-separated PCR products.

13. The method of claim 1, wherein said primer comprises an additional sequence that is not complementary to a region of FMR1 gene promoter.

14. The method of claim 13, wherein the non-complementary region comprises a restriction enzyme site.

15. An isolated primer comprising the sequence ACCGATTCCCAACAACGCGCATA (SEQ ID NO:12).

16. An isolated primer comprising the sequence TTTCGTTATCGTCGTCGTTCGC (SEQ ID NO:13).

17. An isolated primer comprising the sequence ACACACATACACACACTCCCAAA (SEQ ID NO:14).

18. An isolated primer comprising the sequence TTGAAATGGAGTTGAGTGTTTGAT (SEQ ID NO:15).

19. A set of two primer pairs comprising the following sequences:

ACCGATTCCCAACAACGCGCATA (SEQ ID NO:12) and

TTTCGTTATCGTCGTCGTTCGC (SEQ ID NO:13), and

ACACACATACACACACTCCCAAA (SEQ ID NO:14) and

TTGAAATGGAGTTGAGTGTTTGAT (SEQ ID NO:15).

20. A kit comprising, in suitable container means, primer pairs comprising the following sequences:

ACCGATTCCCAACAACGCGCATA (SEQ ID NO:12) and

TTTCGTTATCGTCGTCGTTCGC (SEQ ID NO:13), and

ACACACATACACACACTCCCAAA (SEQ ID NO:14) and

TTGAAATGGAGTTGAGTGTTTGAT (SEQ ID NO:15).

21. The kit of claim 20, further comprising a thermostable DNA polymerase.

22. The kit of claim 20, further comprising sodium bisulfite and hydroquinone.

23. The kit of claim 20, further comprising a DNA denaturing agent.

24. The kit of claim 20, further comprising dNTP's.

* * * * *

UNITED STATES PATENT AND TRADEMARK OFFICE
CERTIFICATE OF CORRECTION

PATENT NO.    :   6,143,504
DATED         :   Nov. 7, 2000
INVENTOR(S)   :   Das et al.

It is certified that error appears in the above-identified patent and that said Letters Patent is hereby corrected as shown below:

On the title page, item [60], Related U.S. Application Data, please insert -- Provisional Application Ser. No. 60/105,892, Oct. 27, 1998.-- therefor.

In claim 3, column 30, line 56, please delete "fluid" and insert -- fluid or -- therefor.

Signed and Sealed this

Twenty-ninth Day of May, 2001

Attest:

NICHOLAS P. GODICI

Attesting Officer

Acting Director of the United States Patent and Trademark Office

SEQUENCE LISTING

```
<160> NUMBER OF SEQ ID NOS: 15

<210> SEQ ID NO 1
<211> LENGTH: 37
<212> TYPE: DNA
<213> ORGANISM: Homo sapiens

<400> SEQUENCE: 1
cggccaaggg tcgtcgcgcg tacgcgcgcg agggtcc                              37

<210> SEQ ID NO 2
<211> LENGTH: 24
<212> TYPE: DNA
<213> ORGANISM: Homo sapiens

<400> SEQUENCE: 2
cagtccgcga gtcgaggcaa agcc                                            24

<210> SEQ ID NO 3
<211> LENGTH: 23
<212> TYPE: DNA
<213> ORGANISM: Homo sapiens

<400> SEQUENCE: 3
gcgcccgccg ccgccactgc ctc                                             23
```

```
<210> SEQ ID NO 4
<211> LENGTH: 37
<212> TYPE: DNA
<213> ORGANISM: Homo sapiens

<400> SEQUENCE: 4
tggctaaggg ttgttgcgcg tatgcgcgcg agggttt                      37

<210> SEQ ID NO 5
<211> LENGTH: 24
<212> TYPE: DNA
<213> ORGANISM: Homo sapiens

<400> SEQUENCE: 5
tagtttgcga gttgaggcaa agct                                    24

<210> SEQ ID NO 6
<211> LENGTH: 23
<212> TYPE: DNA
<213> ORGANISM: Homo sapiens

<400> SEQUENCE: 6
gcgcttgctg ctgctattgc ttt                                     23

<210> SEQ ID NO 7
<211> LENGTH: 37
<212> TYPE: DNA
<213> ORGANISM: Homo sapiens

<400> SEQUENCE: 7
tggttaaggg ttgttgtgtg tatgtgtgtg agggttt                      37

<210> SEQ ID NO 8
<211> LENGTH: 24
<212> TYPE: DNA
<213> ORGANISM: Homo sapiens

<400> SEQUENCE: 8
tagtttgtga gttgaggtaa agtt                                    24

<210> SEQ ID NO 9
<211> LENGTH: 23
<212> TYPE: DNA
<213> ORGANISM: Homo sapiens

<400> SEQUENCE: 9
gtgtttgttg ttgttattgt ttt                                     23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
aggcgctcag ctccgtttcg                                         20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
    Primer

<400> SEQUENCE: 11
agaggtgggc tgcgggcgct                                           20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 12
accgattccc aacaacgcgc ata                                       23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 13
tttcgttatc gtcgtcgttc gc                                        22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 14
acacacatac acacactccc aaa                                       23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15
ttgaaatgga gttgagtgtt tgat                                      24
```